United States Patent [19]

Hasenhuettl

[11] Patent Number: 5,440,027

[45] Date of Patent: Aug. 8, 1995

[54] METHOD FOR PREPARING SACCHARIDE FATTY ACID POLYESTERS BY TRANSESTERIFICATION

[75] Inventor: Gerry Hasenhuettl, Highland Park, Ill.

[73] Assignee: Kraft General Foods, Inc., Northfield, Ill.

[21] Appl. No.: 132,106

[22] Filed: Oct. 5, 1993

[51] Int. Cl.⁶ .................... C07H 1/00; C07H 13/04
[52] U.S. Cl. ................... 536/115; 536/116; 536/119; 536/120; 536/124
[58] Field of Search ........... 536/115, 116, 119, 120, 536/124

[56] References Cited

U.S. PATENT DOCUMENTS

| | | | |
|---|---|---|---|
| 2,853,485 | 9/1958 | Werner et al. | 536/119 |
| 2,893,990 | 7/1959 | Hass et al. | 536/119 |
| 2,931,802 | 4/1960 | Touey et al. | 536/119 |
| 2,938,898 | 5/1960 | Werner et al. | 536/119 |
| 2,948,717 | 8/1960 | Babayan et al. | 536/119 |
| 3,057,743 | 10/1962 | Touey et al. | 536/119 |
| 3,059,009 | 10/1962 | Schmid et al. | 554/208 |
| 3,059,010 | 10/1962 | Schmid et al. | 426/612 |
| 3,093,481 | 6/1963 | Eckey et al. | 536/119 |
| 3,096,324 | 7/1963 | Goins et al. | 536/119 |
| 3,248,381 | 4/1966 | Nobile et al. | 536/119 |
| 3,251,827 | 5/1966 | Schnell et al. | 536/119 |
| 3,353,966 | 11/1967 | Hugenberg et al. | 426/610 |
| 3,378,542 | 4/1968 | O'Boyle et al. | 536/119 |
| 3,480,616 | 11/1969 | Osipow et al. | 536/119 |
| 3,600,186 | 8/1971 | Mattson et al. | 536/119 |
| 3,792,041 | 2/1974 | Yamagishi et al. | 536/119 |
| 3,954,976 | 5/1976 | Mattson et al. | 514/23 |
| 3,963,699 | 6/1976 | Rizzi et al. | 536/119 |
| 4,005,196 | 1/1977 | Jandacek et al. | 514/23 |
| 4,034,083 | 7/1977 | Mattson | 514/53 |
| 4,241,054 | 12/1980 | Volpenhein et al. | 536/115 |
| 4,264,583 | 4/1981 | Jandacek | 514/23 |
| 4,334,061 | 6/1982 | Bossier | 536/119 |
| 4,368,213 | 1/1983 | Hollenbach et al. | 426/590 |
| 4,382,924 | 5/1983 | Berling et al. | 536/119 |
| 4,446,165 | 5/1984 | Roberts | 426/602 |

(List continued on next page.)

FOREIGN PATENT DOCUMENTS

| | | | |
|---|---|---|---|
| 320043 | 6/1989 | European Pat. Off. | C07H 13/06 |
| 0349059A2 | 1/1990 | European Pat. Off. | C08G 63/54 |
| 156263 | 2/1981 | Germany | C07H 13/06 |
| 227137A1 | 10/1984 | Germany | C07H 13/06 |
| 262663A1 | 7/1987 | Germany | C07H 13/06 |
| WO92/03060 | 3/1992 | WIPO . | |

OTHER PUBLICATIONS (Both in German and English) Mieth et al., "On The Synthesis and Characterization of Sucrose Fatty Acid Polyesters". Part 1. On A New Synthesis Procedure [Zur Synthese und charakterisierung von Saccarosefettsäure-polyestern. 1 Mitt. Über ein neues Syntheseverfahren], *Die Nahrung*, pp. 747–751, Aug. 27, 1983.

(List continued on next page.)

*Primary Examiner*—Michael G. Wityshyn
*Assistant Examiner*—Everett White
*Attorney, Agent, or Firm*—Fitch, Even, Tabin & Flannery

[57] ABSTRACT

An improved method for the preparation of saccharide fatty acid polyesters via a two-step process is provided. In the first step, a saccharide is partially esterified so as to contain, on average, between about 1.5 to 3.5 lower acyl ester groups. In the second step, the partially esterified saccharide is reacted with a fatty acid-containing reagent (for example, fatty acids, fatty acid esters, salts of fatty acids, or fatty acid anhydrides) whereby the lower acyl ester groups and the hydroxyl groups on the partially esterified saccharide are replaced with fatty acid ester groups in a transesterification reaction to form a saccharide fatty acid polyesters. The use of a partially esterified saccharide as a reactant in the transesterification reaction allows for a more homogeneous reaction system, less caramelization or other decomposition reactions, and less low molecular weight ester by-product formation. The saccharide fatty acid polyesters, especially the sucrose fatty acid polyesters, are useful as fat substitutes or low-calorie fats in food compositions.

36 Claims, No Drawings

5,440,027
Page 2

U.S. PATENT DOCUMENTS

| | | | |
|---|---|---|---|
| 4,461,782 | 7/1984 | Robbins et al. | 426/549 |
| 4,517,360 | 5/1985 | Volpenhein | 536/119 |
| 4,518,772 | 5/1985 | Volpenhein | 536/119 |
| 4,611,055 | 9/1986 | Yamamoto et al. | 536/119 |
| 4,675,393 | 6/1987 | Coxon | 536/18.6 |
| 4,840,815 | 6/1989 | Meyer et al. | 426/611 |
| 4,931,552 | 6/1990 | Gibson et al. | 536/119 |
| 4,942,054 | 7/1990 | Winter et al. | 426/611 |
| 4,942,228 | 7/1990 | Gibson | 536/119 |
| 4,959,466 | 9/1990 | White | 536/119 |
| 4,973,489 | 11/1990 | Meyer et al. | 426/611 |
| 5,003,057 | 3/1991 | McCurry et al. | 536/18.6 |
| 5,158,796 | 10/1992 | Bernhardt et al. | 426/549 |

OTHER PUBLICATIONS

Akoh et al., "Preparation of Trehalose and Sorbitol Fatty Acid Polyesters by Interesterification", *JAOCS*, vol. 66, No. 9, (Sep. 1989), pp. 1581–1587.

Akoh et al., "Optimized Synthesis of Sucrose Polyesters: Comparison of Physical Properties of Sucrose Polyesters, Raffinose Polyesters and Salad Oils", *Journal of Food and Science*, vol. 55, No. 1, 1990.

Akoh et al., "Synthesis and Properties of Alkyl Glycoside and Stachyose Fatty Acid Polyesters", *JAOCS*, vol. 66, No. 9 (Sep. 1989), pp. 1295–1301.

Linstead et al., "The Stable Form of Sucrose Octaacetate", *J. Amer. Chem. Soc.*, 72, 3260, (1940).

METHOD FOR PREPARING SACCHARIDE FATTY ACID POLYESTERS BY TRANSESTERIFICATION

FIELD OF THE INVENTION

This invention provides an improved method for the preparation of saccharide fatty acid polyesters, especially sucrose fatty acid polyesters, via a two stage process involving intermolecular esterification and transesterification reactions of the acyl ester and hydroxyl groups of a partially esterified saccharide with a fatty acid-containing reagent such as fatty acids, fatty acid esters, salts of fatty acids, and fatty acid anhydrides. The improved method of this invention allows for the preparation of saccharide fatty acid polyesters with less caramelization and with less generation of low molecular weight ester by-products. The reduction of caramelization allows for the formation of products having better (i.e., lighter) color characteristics. The reduction in low molecular weight ester by-products reduces the amount of waste material which must be disposed of or treated for recycling. The sucrose fatty acid polyesters produced by the improved method of this invention are especially useful as fat substitutes in food applications and products.

BACKGROUND OF THE INVENTION

The human consumption of fats in various foodstuffs contributes significantly to obesity. High fat diets also contribute to various human diseases such as heart and coronary diseases. One method of reducing obesity and/or diseases such as heart and coronary diseases in the human population is to reduce the consumption of fat. In recent years, fat substitutes or low-calorie fats have attracted increasing attention as a method of reducing the fat and calorie content of foodstuffs. The objective is to provide edible fats with reduced absorption and digestive properties with minimal side effects and with acceptable taste and feel characteristics when incorporated into food compositions.

Transesterification reactions have been used to prepare saccharide polyesters with reduced absorption and digestive properties. Such transesterification reactions generally required high temperatures and/or toxic solvents (such as dimethylacetamide, dimethylformamide, dimethylsulfoxide, and the like) and were not, therefore, generally suitable for the preparation of fat substitutes for use in food applications.

For example, Rizzi et al., U.S. Pat. No. 3,963,699 (issued Jun. 15, 1976), provided a solvent-free process whereby sucrose and fatty acid lower alkyl esters are simply heated together in an inert atmosphere at or above the melting point of sucrose (about 185° C.). After only a few minutes at 185° C. or above, sucrose begins to decompose which leads to undesirable by-products. This reaction mixture of Rizzi et al. is heterogeneous due to the mutual insolubility of sucrose and the fatty acid lower alkyl esters. Attempts to increase the solubility of sucrose in the transesterification media have generally lead to increased caramelization. Alkali soaps and alkali-free soaps have also been used to retard the rate of sucrose decomposition at the elevated temperatures of the process. Attempts have also been made to improve the yields by employing catalysts and varying reactant ratios (see, e.g., U.S. Pat. Nos. 4,517,360 and 4,518,772). This solvent-free transesterification process has, however, significant problems of its own. For example, the soaps used to retard the thermal decomposition of sucrose must be removed from the reaction products. And even with the addition of such soaps, the products are still contaminated with sucrose decomposition products resulting from thermal cracking or caramelization. The sucrose polyester products are, therefore, often colored (see, e.g., U.S. Pat. Nos. 3,963,699, 4,517,360, 4,518,772, and 4,611,055). Problems are also encountered in attempting to prepare a homogeneous melt of the sucrose and fatty acid ester mixture because the reactants at the reaction temperature are viscous and tend to agglomerate when stirred (see, e.g., U.S. Pat. No. 3,792,041). The sucrose fatty acid ester intermediates that are formed also have a tendency to hydrolyze or saponify under the reaction conditions (see. e.g., U.S. Pat. No. 3,792,041); such side reactions lead to further contamination of the desired sucrose polyester products. The poor affinity of the reactants for one another and the excess of fatty acid esters in the reaction mixture, which is generally necessary to obtain the desired high degree of transesterification, results in a reaction mixture which is susceptible to phase separation (see. e.g., U.S. Pat. No. 4,611,055). Such phase separation will, of course, adversely affect the transesterification reaction.

Akok and Swanson, 55 J. Food Sci., 236 (1990), employed sucrose octaacetate rather than sucrose in a transesterification reaction. Sucrose octaacetate has increased solubility in the fatty acid ester reactants and, therefore, provides a more homogeneous reaction system along with better yields of the sucrose fatty acid polyester and lighter colored products (i.e., reduced caramelization and other decomposition reactions). This procedure, however, generates large amounts of by-product methyl ester (i.e., on average, eight moles of methyl acetate are produced for each mole of sucrose octaacetate reacted). Methyl acetate is a highly flammable material which generally must either be disposed of in an environmentally acceptable manner or converted to acetic acid for reuse or recycling.

More recently, Meyer et al., U.S. Pat. No. 4,840,815 (issued Jun. 20, 1989), and Meyer et al., PCT Publication WO 92/0360 (published Mar. 5, 1992), provided a one-stage, solvent-free, low-temperature, low-pressure process for the preparation of saccharide fatty acid polyesters. The Meyer et al. process involves reacting a mixture of a lower acyl ester saccharide, a fatty acid lower alkyl ester, and an alkali metal catalyst at a reaction temperature of 100° to 125° C. while drawing a vacuum of less than about 15 torr over the reaction mixture. The saccharide fatty acid polyesters are reported to be formed via a transesterification reaction whereby at least a portion of the lower acyl ester groups on the starting saccharide are replaced with the fatty acid groups from the fatty acid lower alkyl ester. Mieth et al., German Patent 227,137 A1 (laid open Sep. 11, 1985), provides a method for preparing polyol-ester mixtures suitable for use as fat substitutes whereby saccharides are esterified or transesterified with short-chain carboxylic acid derivatives in the presence of a catalyst and then reacted with triglycerides having long-chain carboxylic acid derivatives (i.e., pig grease or hard rape fat) at a temperature of 120° to 140° C. The polyol-ester mixtures so produced can be subjected to further transesterification reactions at 100° to 120° C. using longchain carboxylic acids or their esters as reagents. The catalysts used by Mieth et al. include phosphorous acid, alkali metals, alkali alkylates, and alkali salts of weak acids.

It is desirable to provide a new method for the production of saccharide fatty acid polyesters, especially sucrose fatty acid polyesters, which overcome at least some of the problems encountered in the prior art. It is also desirable to provide a new method for the production of saccharide fatty acid polyesters, especially sucrose fatty acid polyesters, which results in less caramelization and/or decomposition products and which generates reduced amounts of by-product low molecular weight esters. The methods of the present invention are generally easier to use and provide better saccharide polyesters than the methods of the prior art. The methods of the present invention generally result in less caramelization and generate significantly less by-product low molecular weight esters during the transesterification reactions.

SUMMARY OF THE INVENTION

The present invention relates to an improved method for preparing saccharide fatty acid polyesters, especially sucrose fatty acid polyesters, via a two-step reaction process. In the first step, a saccharide is converted into a partially esterified saccharide which is more soluble in the hydrophobic reaction mixtures normally used in fatty acid transesterification reactions. In the second step, the partially esterified saccharide is transesterified with a fatty acid-containing reagent selected from the group consisting of fatty acids, fatty acid salts, lower alkyl esters of fatty acids, and fatty acid anhydrides. The improved method of the present invention generally result in less caramelization and generates significantly less by-product low molecular weight esters during the transesterification reactions. The sucrose fatty acid polyesters produced by the improved method of this invention are especially useful as fat substitutes in food applications and products.

The improved process of the present invention involves first reacting a saccharide with an organic acid of formula RCOOH where R is an alkyl group containing 1 to 4 carbon atoms to form a saccharide having, on average, about 1.5 to 3.5, and preferably 2 to 3, lower acyl ester groups (i.e., a partially esterified saccharide). The preferred organic acid for the initial esterification step is acetic acid. The partially esterified saccharide is generally more soluble than the starting saccharide in fatty acid transesterification media and allows, therefore, easier formation of a homogenous reaction media in the next step. In that next step, the partially esterified saccharide is reacted with a fatty acid-containing reagent whereby essentially all the hydroxyl and esters groups in the partially esterified saccharide are replaced with fatty acid ester groups to form a saccharide fatty acid polyester. The transesterification reaction is generally carried out at temperatures of from about 95° to 200° C. under essentially anhydrous conditions. Although not necessary, the relatively low molecular weight, non-fatty acid-containing lower alkyl ester and lower alkyl alcohol by-products can be removed from the reaction system as the reaction proceeds to drive the reaction equilibrium towards the formation of the desired saccharide fatty acid polyester.

The general reactions can be illustrated by the following general reaction scheme using fatty acid esters (i.e., R'COOR") as the fatty acid-containing reagent:

STEP 1:

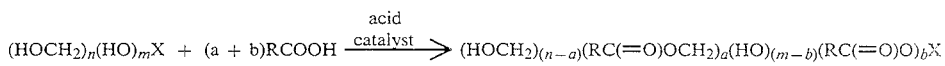

STEP 2:

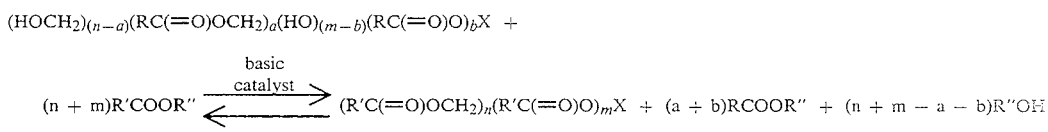

where RC(=O)— represents a lower acyl group where R is an alkyl group having less than 6 carbon atoms, X represents the saccharide backbone, n is the number of hydroxyl groups on the primary carbons in the saccharide backbone, m is the number of hydroxyl groups on the secondary carbons of the saccharide backbone, a is the number of lower acyl groups on primary carbons in the partially esterified saccharide, b is the number of lower acyl groups on secondary carbons in the partially esterified saccharide, the average of the sum (a+b) is between about 1.5 to 3.5 and, preferably, between about 2 and 3, R' is a saturated or unsaturated long chain aliphatic group preferably derived from a fatty acid, and R" is a lower alkyl group having less than six carbon atoms. If desired, the by-products RCOOR" and R"OH can be removed from the reaction mixture of step 2 to drive the equilibrium towards the desired saccharide fatty acid polyester product (R'COOCH$_2$)$_n$(R'COO)$_m$X. The reaction schemes using the other fatty acid-containing reagents would be similar to the one described above taking into account the different structures of the fatty acid-containing reagents.

Preferably the saccharide is sucrose and both R and R" are methyl groups, in which case the by-product RCOOR" is methyl acetate, the by-product R"OH is methanol, and the product (R'COOCH$_2$)$_n$(R'COO)$_m$X is sucrose fatty acid polyester. The by-products methyl acetate and methanol can be removed from the reaction mixture to drive the equilibrium to the right hand side of the equation and towards formation of the sucrose fatty acid polyester.

One object of the present invention is to provide a method for making a saccharide fatty acid polyester comprising:
(1) esterifying hydroxyl groups of a saccharide to form a partially esterified saccharide having, on average, between about 1.5 and 3.5 lower acyl ester groups;
(2) mixing the partially esterified saccharide, a fatty acid-containing reagent, and a transesterification catalyst under essentially anhydrous conditions to form a reaction mixture, wherein the fatty acid-containing reagent is selected from the group consisting of fatty acids, fatty acid salts, lower alkyl esters of fatty acids, fatty acid anhydrides, and mixtures thereof; and (3) heating the reaction mixture to about 95° to 200° C. for a time sufficient to form the saccharide fatty acid polyester.

Another object of the present invention is to provide a method for making a saccharide fatty acid polyester comprising:
(1) esterifying hydroxyl groups of a saccharide to form a partially esterified saccharide having, on average, between about 1.5 and 3.5 lower acyl ester groups;
(2) treating the partially esterified saccharide to reduce the level of free organic acid therein to less than about 0.25 weight percent;
(3) mixing the treated partially esterified saccharide, a fatty acid-containing reagent, and a transesterification catalyst under essentially anhydrous conditions to form a reaction mixture, wherein the fatty acid-containing reagent is selected from the group consisting of fatty acids, fatty acid salts, lower alkyl esters of fatty acids, and fatty acid anhydrides; and
(4) heating the reaction mixture to about 95° to 200° C. for a time sufficient to form the saccharide fatty acid polyester.

Still another object of the present invention is to provide a method for making a saccharide fatty acid polyester comprising:
(1) esterifying hydroxyl groups of a saccharide to form a partially esterified saccharide having, on average, between about 1.5 and 3.5 lower acyl ester groups;
(2) treating the partially esterified saccharide to reduce the level of free organic acid to less than about 0.25 weight percent;
(3) mixing the treated partially esterified saccharide, a fatty acid-containing reagent, and a transesterification catalyst under essentially anhydrous conditions to form a reaction mixture, wherein the fatty acid-containing reagent is selected from the group consisting of fatty acids, fatty acid salts, lower alkyl esters of fatty acids, and fatty acid anhydrides; and
(4) heating the reaction mixture to about 95° to 200° C. for a time sufficient to form the saccharide fatty acid polyester while continuously removing by-product non-fatty acid-containing, low molecular weight ester and alcohol.

These and other objects and advantages of the present invention will become apparent through the following description of the preferred embodiments of the invention.

DESCRIPTION OF THE PREFERRED EMBODIMENTS

The method of the present invention provides an improved method for the preparation of saccharide fatty acid polyesters via an essentially two step reaction process. The present method provides a solvent-free synthesis whereby a saccharide is first partially esterified so as to contain, on the average, between about 1.5 and 3.5 lower alkyl ester groups and then the partially esterified saccharide is then subjected to a transesterification reaction with a fatty acid-containing reagent whereby the lower acyl ester groups and the hydroxyl groups of the partially esterified saccharide are essentially replaced with fatty acid ester groups to yield a saccharide fatty acid polyester. At the transesterification reaction temperature, the partially esterified saccharide and the fatty acid-containing reactant will generally form a homogeneous reaction mixture. The relatively low molecular weight, non-fatty acid-containing lower alkyl ester by-product and the relatively low molecular weight lower alkyl alcohol by-product can, if desired, be removed during the transesterification reaction in order to drive the reaction equilibrium towards completion and the formation of the desired saccharide fatty acid polyester. Generally yields on the order of about 80 to 99 percent can be obtained with reaction times of about four hours.

The partially esterified saccharide can be prepared by conventional means which allow for limited esterification of the hydroxyl groups of a saccharide. It is important that the degree of esterification is such that the partially esterified saccharide contains, on average, between about 1.5 and 3.5 lower acyl ester groups. Preferably, the partially esterified saccharide contains, on average, between about 2 and 3 lower acyl ester groups. Such conventional esterification methods for preparing partially esterified saccharides are described in Linstead et al., *J. Amer. Chem. Soc.*, 62, 3260 (1940) and Coxon, U.S. Pat. No. 4,675,393, both of which are hereby incorporated by reference. By "lower acyl" group it is meant an acyl group of formula $RC(=O)$— where R is an alkyl group having less than 6 carbon atoms. Preferably R is a methyl group.

The partially esterified saccharides can be represented by the general formula

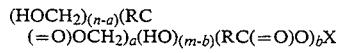

where $RC(=O)$—represents a lower acyl group where R is an alkyl group having less than 6 carbon atoms, X represents the saccharide backbone, n is the number of hydroxyl groups on the primary carbons in the unesterified saccharide backbone, m is the number of hydroxyl groups on the secondary carbons of the unesterified saccharide backbone, a is the number of lower acyl groups on primary carbons in the partially esterified saccharide, b is the number of lower acyl groups on secondary carbons in the partially esterified saccharide. The partially esterified saccharide must have, on average, between about 1.5 and 3.5 lower acyl groups; preferably it has, on average, between about 2 and 3 lower acyl groups. In other words, the average value of the sum (a+b) in the formula of the partially esterified saccharide is between about 1.5 and 3.5 and preferably between about 2 and 3. The individual values of a and b are generally in the range of about 0 to 4 and are independent of each other so long as the average value of the sum (a+b) is within the desired range. For example, if the average value of a is zero, the average value of b must be in the range of about 1.5 to 3.5; if the average value of a is 0.5, the average value of b must be in the range of 1 to 3. Individual molecules of the partially esterified saccharide may have more than four ester groups so long as the average value of (a+b) is in the required range.

It is generally preferred that the partially esterified saccharide is treated to significantly reduce the moisture content and free organic acid content prior to the final transesterification step. Preferably, the free organic acid content of the partially esterified saccharide is reduced to less than about 0.25 weight percent, more preferably to less than about 0.1 weight percent, and most preferably to less than about 0.05 weight percent. Conventional methods to remove moisture and free organic acids can be used. One preferred technique whereby water and free organic acids are removed in a single step is freeze drying.

The saccharide starting materials for the present invention can be monosaccharides, disaccharides, and higher polysaccharides. Suitable monosaccharides include fructose, glucose, galactose, mannose, ribulose, rhamnose, xylulose, xylose, ribose, and arabinose; glucose is the preferred monosaccharide. Suitable disaccharide include melibiose, lactose, maltose, sucrose, trehalose, and cellobiose; sucrose is the preferred disaccharide. Suitable higher polysaccharides include raffinose, gentianose, 4'-galactosyl lactose, trisaccharides of galactose, mannose, glucose, and fructose, stachyose, verbascose, maltodextrins, corn syrup solids, zylans, glycogen, cellulose, amylose, agarose, galactans, and mannans. Sucrose, a non-reducing disaccharide, is the most preferred starting saccharide.

As noted above, the saccharide starting materials are converted to the partially esterified saccharide by esterifying, on average, between about 1.5 and 3.5 of the hydroxyl groups of the saccharide starting materials using conventional methods. For example, sucrose can be partially esterified by reacting with acetic acid and an acid catalyst such as p-toluenesulfonic acid at about 100° C. for about three hours to from a mixture consisting mainly of sucrose diacetate and sucrose triacetate. Other esterification catalysts can also be used. Suitable acid catalysts for the initial esterification step include, for example, p-toluenesulfonic acid, phosphoric acid, polyphosphoric acid, phosphorous pentoxide, sulfuric acid, stannous chloride, zinc oxide, and the like. In the initial esterification step, the acid catalyst is generally used in an amount less than about 5 weight percent and preferably in the range of about 0.5 to 2.5 weight percent.

Generally, the initial esterification step can be carried out at a temperature of about 70° to 95° C. The desired degree of esterification can normally be achieved by reaction times on the order of about 1 to 8 hours. The esterification reaction progress can be followed using, for example, thin layer chromatography or liquid chromatography. After removing excess acetic acid, the partially esterified saccharide is generally ready for use in the next transesterification step. It is generally preferred, however, that the free organic acid content of the partially esterified saccharide is reduced to below about 0.25 weight percent, more preferably below about 0.1 weight percent, and most preferably below about 0.05 weight percent.

Non-reducing saccharides (such as sucrose) can be converted directly into the partially esterified saccharides. Reducing saccharides (having a hydroxyl group alpha to an ether linkage) must first be converted to a non-reducing form prior to the initial esterification reaction; such conversion can be carried out using conventional means. For example, a reducing saccharide can be converted to a non-reducing saccharide by reaction with an alcohol to form a glycoside. Suitable alcohols for converting the reducing saccharides to non-reducing saccharides include, for example, alkyl alcohols, aryl alcohols, alkaryl alcohols, aralkyl alcohols, alkaryl alcohols, heteroalkyl alcohols, heteroaryl alcohols, thio alcohols, and polyalcohols including sugar alcohols. Preferred alcohols are alkyl alcohols containing 1 to 6 carbon atoms with methanol and ethanol being most preferred. Thus, the reducing saccharide glucose can be converted to the non-reducing methyl glucoside by reaction with methanol in the presence of HCl whereby the hydroxyl group alpha to the ether linkage is methylated. Once the non-reducing saccharide is formed, the remaining hydroxy groups may then be esterified in the normal manner to form the partially esterified saccharides.

Both naturally-occurring non-reducing saccharides and non-reducing saccharides prepared from reducing saccharides are employed in the same manner in the present invention. On average, between about 1.5 and 3.5 of the hydroxyl groups in the saccharide must be converted to lower alkyl ester groups for the saccharide to be useful in the present invention. Preferably, between about 2 and 3 of the hydroxyl groups in the saccharide are converted to lower alkyl ester groups. Such partially esterified saccharides generally allow the formation of a homogenous reaction mixture with the fatty acid-containing reagents in the fatty acid transesterification step at the reaction temperatures employed.

Preferred partially esterified saccharides are derived from sucrose and have, on average, between about 1.5 and 3.5 ester groups of the general formula -OOCR, where R is an aliphatic group containing from 1 to 6 carbon atoms, attached to the sucrose backbone in place of the hydroxy groups. More preferred partially esterified saccharides are derived from sucrose and have, on average, between about 2 and 3 ester groups of the general formula -OOCR, where R is an aliphatic group containing from 1 to 6 carbon atoms, attached to the sucrose backbone in place of the hydroxy groups. Preferably, R is a methyl group (i.e., the ester group is acetate). The most preferred partially esterified ester saccharide is derived from sucrose and contains, in large part, sucrose diacetate and sucrose triacetate.

The fatty acid-containing reagents used in the present invention include fatty acids, fatty acid salts, lower alkyl esters of fatty acids, and fatty acid anhydrides. The fatty acids employed in the present invention are of the general formula R'COOH where R' is a saturated or unsaturated aliphatic group generally containing from 3 to about 24 carbon atoms. The fatty acid salts employed in the present invention are of the general formula $R'COO^-Y^+$ where R' is as described above and Y is an cation selected from the group consisting of sodium, potassium, magnesium, calcium, and the like.

The fatty acid lower alkyl esters employed in the present invention are of general formula R'COOR" where R' is as described above and R" is a lower alkyl group having from 1 to about 6 carbon atoms. The fatty acid anhydrides employed in the present invention are of the general formula $(R'CO)_2O$ where R' is as described above; the two R' groups in the fatty acid anhydride can be the same or different. Preferably, R' in the fatty acid-containing reagent is a long chain saturated or unsaturated aliphatic group containing between about 8 to 24 carbon atoms and, most preferably, R' is a long chain saturated or unsaturated aliphatic group containing between about 12 to 22 carbon atoms. Preferably R" is a methyl group. Preferably Y is a sodium or potassium cation.

The fatty acid lower alkyl esters, the fatty acid lower alkyl ester salts, and the fatty acid anhydrides are preferably derived from the corresponding fatty acids. Examples of suitable fatty acids for use directly as fatty acid-containing reagents and for forming the other fatty acid-containing reagents include butyric, caproic, caprylic, capric, lauric, myristic, myristoleic, palmitic, palmitoleic, stearic, oleic, ricinoleic, linoleic, oleosteric, arachidic, behenic, erucic, arachidonic, and lignoceric acids. Generally fatty acids containing between about 14 and 18 carbon atoms are preferred since they are liquid at the reaction temperature and the corresponding fatty acid-containing reagents formed therefrom have minimal volatility at the reaction temperature and conditions employed in the esterification reaction. Pure fatty acids, naturally-occurring fats and oils (such as, for example, found in soybean, safflower, corn, peanut, and cottonseed oils), or partially hydrogenated fats and oils can be used. The fatty acids can be converted to the other corresponding fatty acid reagents using conventional methods. Both single fatty acid-containing reagents and mixtures of fatty acid-containing reagents may be employed in the present invention. Preferred fatty acids include stearic acid, oleic acid, palmitic acid, lauric acid, linoleic acid, and mixtures thereof. Preferred fatty acid lower alkyl esters include methyl stearate, methyl oleate, methyl palmirate, methyl laurate, methyl linoleate, and mixtures thereof. Preferred salts of fatty acid include the sodium and potassium salts of stearic acid, oleic acid, palmitic acid, lauric acid, linoleic acid, and mixtures thereof. Preferred fatty acid anhydrides include stearic acid, oleic acid, palmitic acid, linoleic acid, and mixtures thereof.

Preferably, the fatty acid-containing reagent is selected from the group consisting of fatty acids and fatty acid esters. When fatty acid anhydrides are employed, they are preferably used in combination with the fatty acids and/or fatty acid esters.

Generally, the fatty acid-containing reagent and the partially esterified saccharide are present in the transesterification reaction mixture at a molar ratio of at least about 4 to 1 and preferably at a molar ratio of between about 6 to 1 and 15 to 1. Of course, the desired molar ratio will vary with different saccharides because of the different number of ester and hydroxyl groups present. More preferably, the amounts of the partially esterified saccharide and the fatty acid-containing reagent in the reaction mixture are adjusted so that the molar ratio of the fatty acid-containing reagent to the partially esterified saccharide is about equal to the number of available ester and hydroxyl groups in the partially esterified saccharide. For example, when using partially esterified sucrose containing two acetate groups (with a total of eight reactive groups—two acetate groups and six hydroxyl groups), the molar ratio of the fatty acid-containing reagent to the partially esterified saccharide would preferably be about 8 to 1 (i.e., approximately one fatty acid-containing reagent molecule for each available ester and hydroxyl group in the saccharide). Lower or higher molar ratios can be used if desired within the general guidelines provided above.

The catalysts used for the transesterification reaction include both acid and base transesterification catalysts. Suitable acid catalysts include p-toluenesulfonic acid, phosphoric acid, polyphosphoric acid, phosphorous pentoxide, sulfuric acid, stannous chloride, zinc oxide, and the like. Suitable base catalysts include alkali metals, alkali metal carbonates, alkaline earth carbonates, alkali metal hydrides, alkaline earth hydrides, alkali metal alkoxides, and alkaline earth alkoxides. Generally, acid catalysts are used when the partially esterified saccharide is reacted with fatty acids or fatty acid anhydrides. Generally, base catalysts are used when the partially esterified saccharide is reacted with fatty acid esters. Generally, both acid and base catalysts can be used with salts of fatty acids realizing, of course, that under acidic conditions, the salts will be converted to the corresponding fatty acids.

Preferred alkali metal catalysts include sodium and potassium metal. Preferred alkali metal alkoxide catalyst include sodium and potassium alkoxides, including potassium methoxide, sodium methoxide, potassium ethoxide, sodium ethoxide, potassium t-butoxide, and sodium t-butoxide. Sodium methoxide is generally the most preferred alkali metal alkoxide catalyst. Preferred alkali metal carbonate catalysts include sodium carbonate and potassium carbonate. Preferred alkaline earth hydrides include calcium hydride. Mixtures of base catalysts can also be used if desired. For example, using sodium methoxide and calcium hydride in combination generally provide saccharides fatty acid polyesters having better color properties.

In the transesterification reaction, the acid or base catalyst is generally used in an amount less than about 5 weight percent and preferably in the range of about 1 to 2.5 weight percent. For the highest product yields, the catalyst should be freshly prepared.

The transesterification reaction mixture formed from the basic starting materials (partially esterified saccharide, fatty acid-containing reagent, and catalyst) should be essentially anhydrous. Additionally, as noted above, the partially esterified saccharide preferably is essentially free of organic acids. The transesterification reaction itself is also carried out under essentially anhydrous conditions. Conventional means can be used to insure the required essentially anhydrous reactants and conditions. For example, reactants can be vacuum dried and stored over phosphorous pentoxide or other drying agents. The partially esterified saccharide can be freeze dried to remove both water and free organic acids. The reaction apparatus can be dried by flushing with dried, inert gases.

In the transesterification reaction, the reactants (partially esterified saccharide and fatty acid-containing reagent) and catalyst are mixed in a reaction vessel and then heated to the reaction temperature (about 95° to 200° C. and preferably about 95° to 125° C.). As the transesterification reaction proceeds, the relatively low molecular weight, non-fatty acid-containing lower alkyl ester by-product and the relatively low molecular weight, non-fatty acid-containing lower alkyl alcohol by-product can be, if desired, removed to drive the equilibrium transesterification reaction to completion. Preferably the by-product ester and alcohol are removed continuously by vacuum techniques or by inert gas stripping or sparging.

If the relatively low molecular weight, non-fatty acid-containing lower alkyl ester and alcohol by-products are to be removed (preferably continuously) during the transesterification reaction to drive the equilibrium towards the desired saccharide fatty acid polyester, the reactants are preferably selected so that the relatively low molecular weight, non-fatty acid-containing lower alkyl ester and alcohol by-products (such as methyl acetate and methanol) are relatively volatile and, thus, can be removed relatively easily from the reaction mixture.

One preferred method of removing the by-product ester and alcohol is to continuously draw a vacuum over the reaction mixture. Another preferred method of removing the by-product ester and alcohol is inert gas stripping or sparging; suitable inert gases include nitrogen, argon, and the like. Vacuum techniques, however, generally provide higher product yields. When using vacuum to remove the by-product ester and alcohol, it is generally preferred that the pressure is less than about 500 mm Hg, more preferably less than about 250 mm Hg, more preferably less than about 15 mm Hg, and most preferably less than about 1 mm Hg. When using inert gas stripping, the pressure can be at atmospheric pressure as well as below or above atmospheric pressure. Most preferably, the reaction is run under an inert, reduced-pressure, stream of nitrogen or argon at a vacuum lower than about 1 mm Hg. It is also generally preferred that the vacuum and inert atmosphere be initiated before the reactants are heated to the desired reaction temperature. Generally, as noted above, the reaction temperature for the transesterification step is in the range of about 95° to 200° C.; preferably, the reaction temperature is in the range of about 95° to 125° C.; more preferably, the reaction temperature is in the range of about 105° to 115° C.

The transesterification reaction is continued until sufficient conversion of the partially esterified saccharide to the desired saccharide fatty acid polyester has occurred. Generally a reaction time of about four hours will result in a 80 to 99 percent conversion to the desired product.

Generally, the saccharide fatty acid polyesters produced by this invention are useful as fat substitutes or low-calorie fats. It is generally preferred that essentially all of the ester and hydroxyl groups in the partially esterified saccharide are replaced with fatty acid ester groups in the saccharide fatty acid polyesters. For example, it is preferred that a sucrose polyester produced by the method of this invention be composed mainly of sucrose having about eight fatty acid ester groups.

Once the transesterification reaction is completed, the reaction mixture is allowed to cool and the saccharide fatty acid polyester is collected and, if desired, purified. Conventional purification techniques can be used. It is generally preferred that the reaction mixture is first neutralized (using, for example, acetic acid), dissolved in an organic solvent (for example, hexane), and treated with activated carbon. Alternatively, the saccharide fatty acid polyester can be decolorized using hydrogen peroxide. After removing any added carbon or organic solvents, the desired saccharide fatty acid polyester can be obtained using conventional techniques included, but not limited to, molecular or short-path distillation.

The saccharide fatty acid polyesters of the present invention are especially useful as fat substitutes or low-calorie fats in food products intended for human consumption. These saccharide fatty acid polyesters may be blended or incorporated into food compositions to reduce the overall calorie content of prepared food product. Liquid, semi-solid, or solid saccharide fatty acid polyesters (or combinations thereof) may be employed as fat substitutes. The solid saccharide fatty acid polyesters (i.e., melting points above about 37° C.) may also function as anti-anal leakage agents for use with the liquid saccharide fatty acid polyesters of this invention.

The following examples are provided to illustrate the invention and not to limit the invention. Unless specified otherwise, all percentages given in this specification are by weight.

Example 1

Sucrose (34.2 g; 0.1 moles) can be mixed with acetic acid (50 g; 0.83 moles) and p-toluenesulfonic acid (0.2 g; 0.001 moles). The reaction mixture can then be heated to 100° C. for three hours. Sodium carbonate (0.1 g; 0.001 moles) can be added in order to neutralize the acid catalyst. Excess acetic acid can be removed at reduced pressure in a rotary evaporator. About 40 g of a partially esterified sucrose acetate (about 95 percent yield) containing about 70 weight percent sucrose diacetate and about 15 weight percent sucrose triacetate should be obtained.

Alternatively, the excess acetic acid could be removed by freeze drying the esterification reaction mixture. In such a case, the addition of sodium carbonate could be omitted.

Examples 2

Freeze dried, partially esterified sucrose acetate (42.6 g; 0.1 moles) as described in Example 1 could be mixed with fatty acids from partially hydrogenated soybean oil (223 g; 0.8 moles) and zinc oxide (0.13 g) and then heated to 180° C. while allowing the water to distill from the reaction mixture under slightly reduced pressure (i.e., about 200 to 250 mm Hg). The reaction can be continued until periodic sampling shows no further decrease in the acid number of the reaction mixture; generally, reaction times of about 4 to 6 hours are sufficient. The reaction mixture can then be treated with sodium carbonate (0.1 g; 0.001 moles) and cooled to 60° C. After filtering through a medium porosity sintered glass filter, the filtrate can be distilled at 150° C. and about $1 \times 10^3$ mm Hg in a molecular distillation apparatus. The expected sucrose fatty acid polyester (about 218 g; about 90 weight percent yield) could be collected as the non-volatile residue.

Example 3

Dried, partially esterified sucrose acetate (42.6 g; 0.1 moles) as described in Example 1 could be mixed with fatty acid methyl esters from partially hydrogenated soybean oil (234 g; 0.8 moles). The mixture could be dried at 110° C. and reduced pressure (about 250 mm Hg) for thirty minutes. Sodium methoxide (5.6 g; 0.1 moles) could then be added and the reaction heated at 90° to 120° C. while removing low molecular weight by-products by distillation. The reaction could be continued until distillation of by-product methanol and methyl acetate ends. Acetic acid (5 g; 0.1 moles) could then be added and the reaction mixture cooled to 60° C. After filtering through a medium porosity sintered glass filter, the filtrate could be distilled at 130° C. and about $1 \times 10^{-3}$ mm Hg in a molecular distillation apparatus. The expected sucrose fatty acid polyester (about 184 g; about 90 weight percent yield) could be collected as the non-volatile residue.

That which is claimed is:

1. A method for making a saccharide fatty acid polyester comprising:
   (1) esterifying hydroxyl groups of a saccharide to form a partially esterified saccharide having, on average, between about 1.5 and 3.5 lower acyl ester groups;
   (2) mixing the partially esterified saccharide, a fatty acid-containing reagent, and a transesterification catalyst under essentially anhydrous conditions to form a reaction mixture, wherein the fatty acid-containing reagent is selected from the group consisting of fatty acids, fatty acid salts, lower alkyl esters of fatty acids, fatty acid anhydrides, and mixtures thereof; and (3) heating the reaction mixture to about 95° to 200° C. for a time sufficient to form the saccharide fatty acid polyester.

2. A method as defined in claim 1, wherein the partially esterified saccharide has, on average, between about 2 and 3 lower acyl ester groups and the reaction mixture is heated to about 95° to 125° C.

3. A method as defined in claim 2, wherein the saccharide is sucrose.

4. A method as defined in claim 3, wherein the partially esterified saccharide is sucrose having, on average, 2 to 3 ester groups of general formula -OOCR, where R is an aliphatic group containing from 1 to 6 carbon atoms.

5. A method as defined in claim 2, where the partially esterified saccharide is treated prior to being added to the reaction mixture to reduce the level of free organic acid therein to less than 0.25 weight percent.

6. A method as defined in claim 2, wherein a non-fatty acid-containing lower alkyl ester by-product and a non-fatty acid-containing lower alkyl alcohol by-product are removed from the reaction mixture.

7. A method as defined in claim 6, wherein the non-fatty acid-containing lower alkyl ester by-product and the non-fatty acid-containing lower alkyl alcohol by-product are continuously removed from the reaction mixture by drawing a vacuum of less than about 250 mm Hg over the reaction mixture.

8. A method as defined in claim 7, wherein the vacuum is less than about 15 mm Hg.

9. A method as defined in claim 6, wherein the non-fatty acid-containing lower alkyl ester by-product and the non-fatty acid-containing lower alkyl alcohol by-product are continuously removed from the reaction mixture by sparging with a dry inert gas.

10. A method as defined in claim 2, wherein the fatty acid-containing reagent is a fatty acid or a mixture of fatty acids and the transesterification catalyst is an acid catalyst.

11. A method as defined in claim 10, where the fatty acid-containing reagent is selected from the group consisting of stearic acid, oleic acid, palmitic acid, lauric acid, linoleic acid, and mixtures thereof and the transesterification catalyst is selected from the group consisting of p-toluenesulfonic acid, phosphoric acid, polyphosphoric acid, phosphorous pentoxide, sulfuric acid, stannous chloride, and zinc oxide.

12. A method as defined in claim 2, wherein the fatty acid-containing reagent is a fatty acid ester or a mixture of fatty acid esters and the transesterification catalyst is a base catalyst.

13. A method as defined in claim 12, where the fatty acid-containing reagent is selected from the group consisting of methyl stearate, methyl oleate, methyl palmirate, methyl laurate, methyl linoleate, and mixtures thereof and the transesterification catalyst is selected from the group consisting of alkali metals, alkali metal carbonates, alkaline earth carbonates, alkali metal hydrides, alkaline earth hydrides, alkali metal alkoxides, and alkaline earth alkoxides.

14. A method for making a saccharide fatty acid polyester comprising:
(1) esterifying hydroxyl groups of a saccharide to form a partially esterified saccharide having, on average, between about 1.5 and 3.5 lower acyl ester groups;

(2) treating the partially esterified saccharide to reduce the level of free organic acid therein to less than about 0.25 weight percent;

(3) mixing the treated partially esterified saccharide, a fatty acid-containing reagent, and a transesterification catalyst under essentially anhydrous conditions to form a reaction mixture, wherein the fatty acid-containing reagent is selected from the group consisting of fatty acids, fatty acid salts, lower alkyl esters of fatty acids, and fatty acid anhydrides; and (4) heating the reaction mixture to about 95° to 200° C. for a time sufficient to form the saccharide fatty acid polyester.

15. A method as defined in claim 14, wherein the partially esterified saccharide has, on average, between about 2 and 3 lower acyl ester groups and the reaction mixture is heated to about 95° to 125° C.

16. A method as defined in claim 15, wherein the saccharide is sucrose.

17. A method as defined in claim 16, wherein the partially esterified saccharide is sucrose having, on average, 2 to 3 ester groups of general formula -OOCR, where R is an aliphatic group containing from 1 to 6 carbon atoms.

18. A method as defined in claim 15, wherein a non-fatty acid-containing lower alkyl ester by-product and a non-fatty acid-containing lower alkyl alcohol by-product are removed from the reaction mixture.

19. A method as defined in claim 18, wherein the non-fatty acid-containing lower alkyl ester by-product and the non-fatty acid-containing lower alkyl alcohol by-product are continuously removed from the reaction mixture by drawing a vacuum of less than about 250 mm Hg over the reaction mixture.

20. A method as defined in claim 19, wherein the vacuum is less than about 15 mm Hg.

21. A method as defined in claim 18, wherein the non-fatty acid-containing lower alkyl ester by-product and the non-fatty acid-containing lower alkyl alcohol by-product are continuously removed from the reaction mixture by sparging with a dry inert gas.

22. A method as defined in claim 15, wherein the fatty acid-containing reagent is a fatty acid or a mixture of fatty acids and the transesterification catalyst is an acid catalyst.

23. A method as defined in claim 22, where the fatty acid-containing reagent is selected from the group consisting of stearic acid, oleic acid, palmitic acid, lauric acid, linoleic acid, and mixtures thereof and the transesterification catalyst is selected from the group consisting of p-toluenesulfonic acid, phosphoric acid, polyphosphoric acid, phosphorous pentoxide, sulfuric acid, stannous chloride, and zinc oxide.

24. A method as defined in claim 15, wherein the fatty acid-containing reagent is a fatty acid ester or a mixture of fatty acid esters and the transesterification catalyst is a base catalyst.

25. A method as defined in claim 24, where the fatty acid-containing reagent is selected from the group consisting of methyl stearate, methyl oleate, methyl palmirate, methyl laurate, methyl linoleate, and mixtures thereof and the transesterification catalyst is selected from the group consisting of alkali metals, alkali metal carbonates, alkaline earth carbonates, alkali metal hydrides, alkaline earth hydrides, alkali metal alkoxides, and alkaline earth alkoxides.

26. A method for making a saccharide fatty acid polyester comprising:
  (1) esterifying hydroxyl groups of a saccharide to form a partially esterified saccharide having, on average, between about 1.5 and 3.5 lower acyl ester groups;
  (2) treating the partially esterified saccharide to reduce the level of free organic acid therein to less than about 0.25 weight percent;
  (3) mixing the treated partially esterified saccharide, a fatty acid-containing reagent, and a transesterification catalyst under essentially anhydrous conditions to form a reaction mixture, wherein the fatty acid-containing reagent is selected from the group consisting of fatty acids, fatty acid salts, lower alkyl esters of fatty acids, and fatty acid anhydrides; and
  (4) heating the reaction mixture to about 95° to 200° C. for a time sufficient to form the saccharide fatty acid polyester while continuously removing by-product non-fatty acid-containing, low molecular weight ester and alcohol.

27. A method as defined in claim 26, wherein the partially esterified saccharide has, on average, between about 2 and 3 lower acyl ester groups and the reaction mixture is heated to about 95° to 125° C.

28. A method as defined in claim 27, wherein the saccharide is sucrose.

29. A method as defined in claim 28, wherein the partially esterified saccharide is sucrose having, on average, 2 to 3 ester groups of general formula -OOCR, where R is an aliphatic group containing from 1 to 6 carbon atoms.

30. A method as defined in claim 26, wherein the non-fatty acid-containing lower alkyl ester by-product and the non-fatty acid-containing lower alkyl alcohol by-product are continuously removed from the reaction mixture by drawing a vacuum of less than about 250 mm Hg over the reaction mixture.

31. A method as defined in claim 30, wherein the vacuum is less than about 15 mm Hg.

32. A method as defined in claim 26, wherein the non-fatty acid-containing lower alkyl ester by-product and the non-fatty acid-containing lower alkyl alcohol by-product are continuously removed from the reaction mixture by sparging with a dry inert gas.

33. A method as defined in claim 26, wherein the fatty acid-containing reagent is a fatty acid or a mixture of fatty acids and the transesterification catalyst is an acid catalyst.

34. A method as defined in claim 33, where the fatty acid-containing reagent is selected from the group consisting of stearic acid, oleic acid, palmitic acid, lauric acid, linoleic acid, and mixtures thereof and the transesterification catalyst is selected from the group consisting of p-toluenesulfonic acid, phosphoric acid, polyphosphoric acid, phosphorous pentoxide, sulfuric acid, stannous chloride, and zinc oxide.

35. A method as defined in claim 26, wherein the fatty acid-containing reagent is a fatty acid ester or a mixture of fatty acid esters and the transesterification catalyst is a base catalyst.

36. A method as defined in claim 35, where the fatty acid-containing reagent is selected from the group consisting of methyl stearate, methyl oleate, methyl palmirate, methyl laurate, methyl linoleate, and mixtures thereof and the transesterification catalyst is selected from the group consisting of alkali metals, alkali metal carbonates, alkaline earth carbonates, alkali metal hydrides, alkaline earth hydrides, alkali metal alkoxides, and alkaline earth alkoxides.

* * * * *